(12) United States Patent
Achtman et al.

(10) Patent No.: US 7,235,242 B2
(45) Date of Patent: Jun. 26, 2007

(54) IGA1 PROTEASE FRAGMENT AS CARRIER PEPTIDES

(75) Inventors: Mark Achtman, Berlin (DE); Monique Moreau, Lyons (FR)

(73) Assignees: Max-Planck-Gesellschaft zur Forderung der Wissenschaften E.V. (DE); Pasteur Mérieux Sérums et Vaccins S.A. (FR)

( * ) Notice: Subject to any disclaimer, the term of this patent is extended or adjusted under 35 U.S.C. 154(b) by 0 days.

(21) Appl. No.: 10/841,324

(22) Filed: May 7, 2004

(65) Prior Publication Data

US 2004/0203108 A1 Oct. 14, 2004

Related U.S. Application Data

(62) Division of application No. 09/142,970, filed as application No. PCT/EP98/00294 on Jan. 20, 1998, now abandoned.

(30) Foreign Application Priority Data

Jan. 21, 1997 (EP) ................... 97100883

(51) Int. Cl.
*A61K 39/00* (2006.01)
*A61K 39/02* (2006.01)
*A61K 39/12* (2006.01)
*A61K 39/385* (2006.01)
*C07K 1/00* (2006.01)

(52) U.S. Cl. ............... 424/185.1; 424/190.1; 424/192.1; 424/193.1; 424/197.11; 424/203.1; 424/249.1; 424/250.1; 424/256.1; 530/300; 530/350

(58) Field of Classification Search .......... 424/234.1, 424/185.1, 190.1, 192.1, 193.1, 197.11, 203.1, 424/249.1, 250.1, 256.1; 530/350, 300
See application file for complete search history.

(56) References Cited

U.S. PATENT DOCUMENTS 5,268,270 A 12/1993 Meyer et al.

FOREIGN PATENT DOCUMENTS

| EP | 0 254 090 A1 | 1/1988 |
| EP | 0 326 111 A1 | 8/1989 |
| EP | 0 429 816 A1 | 6/1991 |
| WO | WO 90/11367 | 10/1990 |

OTHER PUBLICATIONS

Poulsen et al. 1989, Infect. Immun., 57(10): 3097-3105.
Pohlner et al., 1987, Nature, 325: 458-462.
International Search Report dated Jul. 23, 2998.
Lomholt, Hans, *Molecular Microbiology* 15(3): 495-506, 1995.
Siber, G.R., *Science* 265: 1385-1387, 1994.
Romero, J.D. et al., *Clinical Microbiology Reviews* 7(4): 559-575, 1994.
Lomholt, H., *APMIS* 104:5-28, 1996.

*Primary Examiner*—Mark Navarro
(74) *Attorney, Agent, or Firm*—Morgan Lewis & Bockius, LLP

(57) ABSTRACT

The present invention is concerned with a fragment of IgA1-protease having 40 to 200 amino acid residues and comprising at least 40 amino acids of an amino acid sequence as shown in SEQ ID NO:1, beginning with the amino acid in any one of positions 1 to 5 and ending with an amino acid in any one of positions 40 to 104 or a homologous sequence, its use as a carrier for a conjugate, particularly in combination with a polysaccharide, and a process for producing the peptide as well as vaccines comprising said peptide.

12 Claims, No Drawings

IGA1 PROTEASE FRAGMENT AS CARRIER PEPTIDES

This is a divisional of U.S. patent application Ser. No. 09/142,970 filed on Apr. 2, 1999, now abandoned, which is the 371 national phase of International Patent Application No. PCT/EP98/00294 filed on Jan. 20, 1998 and claiming priority to European Patent Application No. 97100883.4.

FIELD OF THE INVENTION

The present invention is concerned with a new peptide, its use as a carrier for a conjugate, particularly in combination with a polysaccharide, and a process for producing the peptide as well as vaccines comprising said peptide.

BACKGROUND OF THE INVENTION

Polysaccharides are present as capsules in gram-positive and gram-negative bacteria and as a constituent of the cell wall of bacteria and fungi. Various species of the genera *Neisseria*, *Streptococcus*, *Klebsiella*, *Salmonella*, *Shigella* and *Haemophilus* are pathogenic and are responsible for various human diseases, for example epidemic meningitis, otitis, pneumonia and diarrhoea. These diseases represent a serious global childhood public health problem and therefore, it is important to have a prophylaxis against these diseases.

The polysaccharide macromolecules are comprised of saccharide units which can mediate immunogenicity. Therefore, bacterial polysaccharides or parts thereof have been used for the immunisation of humans. Although, these vaccines are immunogenic in children and adults and can induce protective antibodies, they are not suitable to protect infants because they can only elicit a T-cell independent immune response. Thus, the contact with capsular polysaccharides does not induce a memory response and does not result in a persistent protection. Moreover, it is not possible to elicit an immune response in infants.

To overcome the problem of a T-cell independent immune response, a covalent conjugation of polysaccharides as T-independent antigens to protein carriers as T-dependent antigens has been used and found successful in overcoming this deficiency. Immunisation with such conjugates elicits a T-cell dependent antibody response. However, the choice of carrier proteins which are useful for humans is very restricted, and in most cases, polysaccharides have been coupled to tetanus toxoid, cholera toxoid or diphtheria toxoid. The unlimited or excessive use of these toxoids as carriers is thought to suppress subsequent responses to a polysaccharide coupled to this type of carrier. This suppression of immune response by pre-existing antibodies to the carrier is expected to become a problem in the future.

A further problem which limited the choice of a new carrier protein with regard to this type of conjugate is that the protein has to be non-toxic or detoxified.

Furthermore, known peptide-polysaccharide conjugates suffer from the disadvantage that it is necessary to use an adjuvant to enhance the immune response. However, many known adjuvants are not applicable for humans because they can elicit an inflammatory response. To date, only one adjuvant is permitted for humans: aluminum gel.

SUMMARY OF THE INVENTION

Therefore, it was the object of the present invention to provide new carrier molecules which are highly immunogenic, can elicit a T-cell dependent immune response, result in a long-persisting memory in mammals and possibly avoid the use of adjuvants. This object and further objects which will become apparent from the following description are achieved by the use of a novel peptide having at least 40 amino acids.

DETAILED DESCRIPTION OF THE INVENTION

Therefore, according to a first aspect the present invention provides a peptide having 40 to 200 amino acid residues which comprises at least 40 amino acids of an amino acid sequence as shown in SEQ ID No 1, beginning with the amino acid in any one of positions 1 to 5 and ending with an amino acid in any one of positions 40 to 104 or a homologous sequence.

In a further aspect of the present invention these novel peptides are used as carrier for a conjugate.

Surprisingly, it has been found that a peptide comprising at least 40 N-terminal amino acids of one of SEQ ID No 1, 2, 3, 4 or 5, which are part of an IgA1 protease from *Neisseria* or a homologous sequence, could be used as carrier for an antigen to elicit a T-cell dependent immune response with long persistence even without the use of adjuvant. It was not foreseeable that such a small peptide could be useful as a carrier for an immunogenic conjugate.

The use of this small peptide has many advantages with regard to those carriers used to date. Being only a small peptide, it can be produced synthetically, it can be conjugated to all types of compounds which are used as immunogens, such as polysaccharides and is especially useful in combination with a polysaccharide from *Neisseria*, particularly from *N. meningitidis*, or *Haemophilus*, particularly *H. influenzae*. Therefore, it is useful for producing vaccines for infants as well as for young children and adults.

The peptide of the present invention is part of an IgA1 protease produced by pathogenic bacteria of the genus *Neisseria*. IgA1 protease is an enzyme which degrades IgA1 antibodies produced by the host as protection against the bacteria. Although it was known that IgA1 proteases can elicit an immune response, the use of such a protease as carrier has not been contemplated because on the one hand, it is a large molecule, and on the other hand, it has a negative influence on the immune system of the human to be immunised. In contrast thereto, the peptide does not have this enzymatic effect.

The peptide of the present invention comprises at least 40 amino acids, preferably at least 50 amino acids, more preferably at least 70 amino acids, and most preferably all 104 amino acids of one of the sequences of SEQ ID No 1, 2, 3, 4 or 5 or a homologous sequence thereof. Most preferably, the peptide is the 104mer of SEQ ID No 1.

The peptide can also have more than 104 amino acids. The sequences illustrated in SEQ ID No. 1, 2, 3, 4 and 5 can be extended by further amino acids which do not interfere with other amino acids, affect the T-epitope or alter the structure of the first 40 N-terminal amino acids of the peptide. The sequence can be extended on the N-terminus as well as on the carboxy terminus. The peptide must have at least 40 amino acids and not more than about 200 amino acids. If the peptide has less than 40 amino acids, it is not suitable as carrier and a persistent immunisation is unlikely to occur with it as carrier. On the other hand, a peptide having more than 200 amino acids is difficult to synthesize. It has been found that a peptide having more than 70 amino acids has improved antigenicity, and most preferred is a peptide having 104 amino acids with the sequence of SEQ ID No 1. The said sequence is part of an IgA1 protease from *Neisseria meningitidis*, serogroup A, subgroup III, strain Z3906 and is identical to a sequence with Genbank accession X82474.

The peptide of the present invention is preferably identical or homologous to a peptide having the amino acid sequence of one of SEQ ID No 1, 2, 3, 4 or 5. Preferably, the peptide is at least 85% identical to one of the above-mentioned amino acid sequences, more preferably it is 90% identical and particularly preferred is 95% identical to the above-mentioned amino acid sequences. In the most preferred embodiment, the peptide is 100% identical to the above-mentioned amino acid sequences, particularly to SEQ ID No 1.

A peptide having a sequence homologous to one of the sequences shown in SEQ ID No 1, 2, 3, 4 or 5 is also within the scope of the present invention. SEQ ID No 2 is a sequence from *N. meningitidis*, serogroup C, ET-37 complex, strain Z4400. SEQ ID No 3 is a sequence from *N. meningitidis*, serogroup. A, subgroup III, strain Z3524. SEQ ID No 4 is derived from sequence S09386 from SwissProt. SEQ ID No 5 is a sequence from *N. gonorrhoeae*, strain MS11, published in EP-A 254090 and identical to GenBank accession number A02796.

The term "homologous", as it is used in the present description and claims, refers to a sequence that is at least 80% identical to the respective sequence. The homology of a peptide is typically measured using sequence analysis software (e.g. sequence analysis software package of the Genetics Computer Group, University of Wisconsin Biotechnology Center, 1710 University Avenue, Madison, Wis., 53705). Similar amino acid sequences are aligned to obtain the maximum degree of homology. To this end, it may be necessary to artificially introduce gaps into the sequence. Once optimal alignment has been set up, the degree of homology is established by recording all of the positions in which the amino acids of both sequences are identical, relative to the total number of positions.

Analogs of the peptide of the present invention accordingly are also within the scope of the present invention. An "analog" peptide is an alternate form of a peptide that is characterized as having a substitution, deletion or addition of one or more amino acids that does not alter the biological function of the polypeptide. The biological function of the peptide of the present invention is eliciting a T-dependent immune response when used as carrier together with an antigen.

In a preferred embodiment, the peptide of the present invention comprises additionally a cysteine residue. The cysteine residue can be located either at the carboxy terminus, at the N-terminus or within the amino acid chain by substituting one of the amino acids in the sequence by a cysteine residue. This substitution can be done at all places with the proviso that the T-dependent epitope is not destroyed or affected. Preferably, the cysteine is added at one of the termini. As the peptide having a sequence according to one of SEQ ID No 1, 2, 3, 4 or 5 does not contain any cysteine, the introduction of a cysteine is particularly useful, because it does not destroy or interfere with the structure of the peptide. The cysteine is introduced for a stable coupling with a linker molecule. It is also possible to couple the peptide via other functional groups, for example the amino group of a lysine residue or the carboxylic group of a glutamic or aspartic acid group.

The peptide of the present invention can be produced by microbiological methods as well as by organic synthesis. In a preferred embodiment, the peptide is produced either using recombinant techniques or by synthesis. For the recombinant production of the peptide a polynucleotide is provided on the basis of the amino acid sequence given in one of SEQ ID No 1, 2, 3, 4 or 5 and the peptide is produced according to well-known techniques of genetic engineering.

The other preferred method for producing the peptide of the present invention is via an organic synthesis. The peptide can be synthesized by methods well-known to the skilled artisan. For example, some smaller fragments can be produced by coupling the appropriate amino acids. The complete peptide is then obtained by coupling these fragments.

Therefore, a further aspect of the present invention is a process for producing the peptide using an organic synthesis. In a preferred embodiment the complete peptide is produced by a solid phase synthesis preferably using Fmoc or Boc chemistry. It is especially preferred to carry out the synthesis with an automated peptide synthesizer and to use FastMoc chemistry.

In a particularly preferred embodiment, the 104mer of SEQ ID No 1, the sequence of which is outlined above, is synthesized using an automated peptide synthesizer and FastMoc chemistry wherein the solid phase is TentaGel S RAM Spezial, wherein the amino acids are FMoc protected and the side groups preferably are protected as follows: the carboxyl or hydroxyl group, respectively, of aspartic acid, glutamic acid, serine, threonine and tyrosine with O-t-butyl; the amino or imino group, respectively, of histidine, asparagine and glutamine with trityl; the amino group of lysine with t-butyloxycarbonyl; and the imino group of arginine with PMC. At cycles 1–2, 4, 10–13, 17, 27, 32, 49, 59, 66, 75–78, 84–85, 88, 96–97 and 104–105 double couplings should be performed and free amino groups are blocked by acetylation with acetic anhydride. The activation and coupling is preferably done in the presence of HBTU/diisopropylethylamine. After piperidine deprotection the final product is N-terminally acetylated using acetic anhydride.

The above outlined process, of course, may also be employed if the peptide of the present invention has less than 104 amino acids or more than 104 amino acids. In the former case, the process is varied by omitting some of the first cycles whereas in the latter case, the process is varied by adding some further cycles to introduce further amino acids. If the peptide is a homologous peptide or has a sequence as identified in one of SEQ ID No 2, 3, 4 or 5 or is homologous to one of these sequences, having some different amino acids, the process can be adapted accordingly by using the appropriate amino acid in protected form for the respective cycle.

The peptide of the present invention is a useful carrier for immunoreactive molecules such as polysaccharides. The peptide provides T-cell epitopes which are necessary for generating an immunologic "memory" and therefore generally can be used as carrier for all known immunoreactive molecules to produce conjugates which can be used as efficient vaccines.

In a preferred embodiment of the present invention, the peptide is used as carrier for a polysaccharide to elicit an immune response. The polysaccharide can be any polysaccharide which is known to be immunogenic in mammals, especially humans. The term "polysaccharide" also embraces smaller polysaccharides which are immunogenic and which are sometimes referred to as oligosaccharides. Polysaccharides which can be used as part of the conjugate are capsular polysaccharides, lipopolysaccharides, O-antigens, bacterial or fungal membrane polysaccharides or depolymerized parts thereof, for example polysaccharide C of *Neisseria meningitidis*. The polysaccharide can have a molecular weight in the range of 10,000 to 500,000. Natural occurring polysaccharides normally have a molecular weight in the range of 100,000 to 500,000 whereas depolymerized forms thereof may have a lower molecular weight as low as 10,000.

A further object of the present invention is a conjugate comprising a peptide as described above and an immunoreactive molecule. In a preferred embodiment, the immunoreactive molecule is coupled to the peptide via a linker. The linker provides functional groups at both ends which provide for the bonding to the peptide and the antigenic molecule, respectively. Both functional groups are connected to a bridge, the length of which is chosen so that both parts are presented to the immune system in an optimal manner. The bridge should not be too short as otherwise steric hindrance could occur. On the other hand, it should not be too long so as not to interfere with the structure of both parts. It is preferred that the length of the bridge between both functional groups is 2 to 20 atoms selected from C, N, O and S. More preferably the bridge is selected from $C_2$–$C_8$-alkylene, phenylene, $C_7$–$C_{12}$-aralkylene, $C_2$–$C_6$-alkanoyloxy and benzylcarbonyloxy.

The functional groups used for the coupling to the peptide and the polysaccharide are those functional groups which are commonly used in this field. A review of coupling methods is found in W. E. Dick and M. Beurret in Conjugates Vaccines, J. M. Cruse, R. E. Lewis Jr Eds, Contrib. Microbiol. Immunol. Basel, Karger (1989) 10:48. The peptide is bonded to the linker via a functional group provided by one of the amino acids, for example an amino, a carboxy or hydroxy group. In a preferred embodiment, the peptide is bonded to the linker via the thiol group provided by a cysteine residue. The immunoreactive molecule can be bonded to the spacer via functional groups which are available. In a preferred embodiment when using a polysaccharide as immunoreactive molecule, hydroxy, amino or carboxy groups which are present or have been introduced in the saccharide units are used for the coupling. Preferably, the linker is bonded to the hydroxy groups of the polysaccharide via an ether, ester, amide or carbamate linkage, to the amino groups via a N—OH-succinimidyl linkage and/or to the carboxyl groups via an ester linkage. The conjugate of the present invention can be produced using methods known to the skilled artisan.

The immune response which is elicited by the conjugate of the present invention is dependent on the number and availability of T-cell dependent and B-cell dependent epitopes and their ratio. In the conjugate of the present invention the T-cell dependent epitopes are provided by the peptide whereas the B-cell dependent epitopes are contributed by the polysaccharide. Therefore, the ratio of both parts of the conjugate is an essential feature. Thus, the ratio of both components should be adjusted so that not too little of either sort of molecule is present. It has been found by the inventors of the present invention that good results can be obtained if about 1 mol of peptide is present per 1 to 50 moles, preferably 3 to 30 moles and most preferably 5 to 20 moles of repeating units of the polysaccharide. If less than 1 mol of peptide per 50 moles of repeating units is present, no immune response can be detected because there are not enough peptide molecules to induce a persistent immune response. On the other hand, if more than 1 mol of peptide per mol of repeating units are present, the results are also not satisfying because too much of the polysaccharide is sterically hindered to elicit an immune response. The term "repeating units" refers to units within the polysaccharides which are composed of 1 to 7 different saccharides and differ with regard to the nature of saccharide, linkage position and the anomeric configuration of the saccharide.

A further aspect of the present invention is a vaccine which comprises a conjugate according to the present invention together with conventional carriers, excipients and diluents. The conjugate is mixed with or diluted in or dissolved in a conventional carrier, excipient or diluent as it is known in this field in an efficient amount. This vaccine can be used to immunise infants, children and adults. It is especially useful for the control of epidemically occurring diseases which are caused by Neisseria meningitidis or other bacteria carrying capsular polysaccharides. The use of the vaccine of the present invention results in high antibody titers.

EXAMPLE 1

Production of a synthetic 105mer peptide having the following sequence (SEQ ID No. 1+N-terminal cysteine):
Cys Leu Tyr Tyr Lys Asn Tyr Arg Tyr Tyr Ala Leu Lys Ser Gly Gly Ser Val Asn Ala Pro Met Pro Glu Asn Gly Gln Thr Glu Asn Asn Asp Trp Ile Leu Met Gly Ser Thr Gln Glu Glu Ala Lys Lys Asn Ala Met Asn His Lys Asn Asn Gln Arg Ile Ser Gly Phe Ser Gly Phe Phe Gly Glu Glu Asn Gly Lys Gly His Asn Gly Ala Leu Asn Leu Asn Phe Asn Gly Lys Ser Ala Gln Asn Arg Phe Leu Leu Thr Gly Gly Thr Asn Leu Asn Gly Lys Ile Ser Val Thr Gln Gly The peptide was synthesised using FastMoc chemistry with an automated peptide synthesiser (model 431A, Applied Biosystems). The solid phase was a Rink resin (0.13 mM TentaGel S RAM Spezial, 0.15 mM g$^{-1}$, Rapp Polymere, Tübinqen, Germany) which yields a C-terminal amide capped peptide. The amino groups of the amino acids used for the synthesis were protected with 9-fluorenylmethyloxycarbonyl (Fmoc) groups and side groups were protected with the following groups:

for the carboxyl or hydroxyl group, respectively, of aspartic acid, glutamic acid, serine, threonine and tyrosine: the O-t-butyl group;

for the amino or imino group, respectively, of histidine, asparagine and glutamine: the trityl group;

for the amino group of lysine: the t-butyloxycarbonyl group;

and for the imino group of arginine: the PMC group.

The activation and coupling were done in the presence of 2-(1 H-benzotriazol-1-yl)-1,3,3-tetramethyluronium hexafluorophosphate (HBTU)/diisopropylethylamine. At cycles 1–2, 4, 10–13, 17, 27, 32, 49, 59, 66, 75–78, 84–85, 88, 96–97 and 104–105, double coupling was performed and free amino groups were blocked by acetylation with acetic anhydride. After the last cycle, the peptide was deprotected with piperidine and the final product was N-terminally acetylated using acetic anhydride.

The side-chain deprotection and cleavage from the resin support was carried out with 2.1% (v/v) 1,2-ethanedithiol, 4.2% (v/v) thioanisol, 4.2% (v/v) water, 6.2% phenol (v/v) and 83% (v/v) trifluoroacetic acid (TFA) for 3 hours at room temperature. The resin was removed by filtration and triethylsilane was added in dropwise fashion until the solution was colourless. The solution was then incubated 3 more hours at room temperature. 360 mg crude peptide was recovered after precipitation with t-butylmethylether followed by centrifugation and lyophilisation. 130 mg of the crude peptide was dissolved in 40 ml 50 mM ethylmorpholine, pH 8.3 containing 50 mM dithiothreitol and incubated overnight at room temperature. The pH was adjusted to 3.5 with 10% TFA and the peptide was purified by reverse phase HPLC (Pep-S, C2/C18, 100 Å pore size, 12 µm 22.5 mm×25 cm, Pharmacia) using a gradient (25 to 45% (v/v)) of acetonitrile, 0.1% TFA (10 ml min$^{-1}$, gradient of 0.33% min$^{-1}$). The peptide eluted as one peak at about 25% acetonitrile, and the peak was lyophilized (73 mg) before further use. An analysis by HPLC and mass spectrometry showed that over 65% of the final product corresponded to the desired sequence. The N-terminal sequence was confirmed by N-terminal Edman sequencing of the sample removed before N-terminal acetylation.

EXAMPLE 2

Preparation of a Polysaccharide Peptide Conjugate

A dry powder of capsular polysaccharide from *Neisseria meningitidis* serogroup C, referred to as polysaccharide C in the following, was obtained by an extraction process as described by E. Gotschlich et al. in J. Exp. Med., No 129 (1969), p 1349–1365. 100 mg of polysaccharide C were dissolved in 0.2 M NaCl to a final concentration of 11.1 mg/ml (solution A). In parallel, a solution of 0.2 M adipic acid dihydrazide (ADH) in 0.2 M NaCl was prepared (solution B). A 0.5 M solution of ethyl dimethyl aminopropyl carbodiimide (EDAC) in 0.2 M NaCl was also prepared (solution C). 9 ml of solution of A, 10 ml of solution B and 1 ml of solution C are mixed together to give a preparation containing 5 mg/ml of polysaccharide C, 0.125 M ADH and 0.025 M EDAC. 0.1 M HCl was added to adjust the pH to 6.5; this pH was maintained during the entire reaction period of 45 minutes. The temperature was about 20° C.

Reaction was stopped by 40 µl 0.1 N NaOH which raised the pH to 7.1. The reaction mixture was dialysed against 0.5 M NaCl, 10 mM phosphate and then water and subsequently lyophilized.

The size of the derivatized polysaccharide C was controlled on a HPLC exclusion column TSK 4000 (manufacturer Tosohaas). The results demonstrated that no depolymerization had occurred in the course of the derivatization.

During the derivatization, about 3.4% of repeat units were derivatized with an $NH_2$ group.

The lyophilized product was dissolved in 0.02 M phosphate buffer, pH 7, to a concentration of 6.25 mg/ml and degassed. Succinimidyl maleiimido butyrate (GMBS) was dissolved in dimethylsulfoxide (DMSO) under nitrogen at a concentration of 25 mg/ml and then added to derivatised polysaccharide C in equal amount. The reaction mixture was stirred for 90 minutes at room temperature under nitrogen. The activated polysaccharide C was purified by sephadex G50 exclusion column chromatography. The excluded fraction was recovered and concentrated to about 7.5 mg/ml by ultrafiltration (30K Amicon membrane). The concentrated solution was degassed.

20 mg of the peptide as obtained in example 1 was dissolved in water at a concentration of 10 mg/ml under nitrogen. 1.5 ml of the peptide solution was added to 1.2 ml of the preparation containing the activated polysaccharide C, so that the ratio (maleiimido residues)/(thiol residues) equaled 2. The reaction mixtures were maintained over night under stirring at room temperature. Then the unreacted maleiimido residues were inactivated by adding 0.010 ml mercaptoethanol.

The conjugated product was purified on a 4BCL Sepharose column. The eluted fractions were assayed for the presence of saccharides (sialic acid) and peptides. Fractions responding positively in both assays were pooled.

The amount of sialic acid residues was determined according to the dosage method described in Svennerholm L., Biochim. Biophys. Acta (1957) 24:604, and the amount of peptide was determined according to the method of Lowry et al, J. Biol. Chem. (1951) 193:265. It was shown that the ratio (peptide)/(repeating units of polysaccharide C) mole/mole was 1:18 (corresponding to a ratio weight/weight of 1.8:1).

EXAMPLE 3

A dry powder of capsular polysaccharide from *Streptococcus pneumoniae* type 4, referred to as polysaccharide Pneumo 4 in the following, is obtained by an extraction process as described in the patent WO-A 82/01 995 "Procédé de purification de polyosides de *Streptococcus pneumoniae* et vaccins à base de polyosides ainsi purifiés". 100 mg of polysaccharide Pneumo 4 were dissolved in 0.2 M NaCl to a final concentration of 11.1 mg/ml (solution A). In parallel, a solution of adipic acid dihydrazide (ADH) in 0.2 M NaCl was prepared in a concentration of 0.25 M (solution B). A solution of ethyl dimethyl aminopropyl carbodiimide (EDAC) in 0.2 M NaCl was also prepared at a concentration of 0.5 M (solution C). 9 ml of solution A, 10 ml of solution B and 1 ml of solution C are mixed together to give a preparation containing 5 mg/ml of polysaccharide Pneumo 4, 0.125 M ADH and 0.025 M EDAC. 1 N HCL was added to a pH of 4.9; this pH was maintained during the entire reaction period of 30 minutes. The temperature was about 25° C.

Reaction was stopped by 0.28 ml N NaOH. The pH was increased to 7.5. The reaction mixture was dialysed against 0.5 M NaCl and then water and subsequently lyophilized.

The size of the derivatized polysaccharide Pneumo 4 was controlled on a HLPC exclusion column TSK 4000 (manufacturer Tosohaas). No depolymerization occurred in the course of the derivatization.

During the derivatization, about 8.2% of repeat units of the polysaccharide Pneumo 4 were derivatized with a $—NH_2$ group.

Lyophilized product was dissolved in 0.05 M NaCl at a concentration of 2.76 mg/ml and degassed. Succinimidyl maleiimido butyrate (GMBS) was dissolved in dimethylsulfoxide (DMSO) under nitrogen at a concentration of 25 mg/ml. 1.75 ml of the GMBS solution were added to 16 ml of the polysaccharide solution under nitrogen. The reaction mixture was left under stirring for 5 hours at room temperature under nitrogen. The activated polysaccharide Pneumo 4 was purified on an exclusion column Sephadex G50. The excluded fraction was recovered and concentrated to about 7 mg/ml on a 30K membrane (Amicon). The concentrated solution was degassed.

20 mg of the peptide as obtained in example 1 were dissolved in 0.1 M NaCl, 0.01 M phosphate buffer pH 7.5, at a concentration of 4.6 mg/ml under nitrogen. On the one hand, 2.2 ml of the peptide solution were added to 1.25 ml of the preparation containing the activated polysaccharide Pneumo 4, so that the ratio (maleiimidyl residues)/(thiol groups) equalled 1 (Pneumo 4-peptide-1 conjugate). Reaction mixtures were maintained 6 hours under stirring at room temperature under nitrogen, then overnight at +4° C. Then the unreacted maleiimidyl residues were inactivated by adding 0.005 ml mercaptoethanol to each reaction mixture.

The conjugates were purified on a Sepharose 4BCL column. The eluted fractions were assayed for the presence of sugars and peptides. Fractions responding positively in both assays were pooled.

The amount of sugar was determined according to the dosage method described in Dubois et al. Anal. Chem. (1956) 3:350, and the amount of peptide was determined according to the method of Lowry et al, J. Biol. Chem. (1951) 193: 265. The ratio of repeat units of peptide/ polysaccharide mole/mole is 1:30 for the Pn 4-peptide-1 conjugate (corresponding to a ratio w/w of 0.4:1).

EXAMPLE 4

A dry powder of capsular polysaccharide from *Neisseria meningitidis* serogroup A, referred to as polysaccharide A in the following, is obtained by an extraction process as described by E. Gotschlich et al. in J. Exp. Med., No 129 (1969), p 1349–1365 100 mg of polysaccharide A were dissolved in water to a final concentration of 5 mg/ml (solution A). In parallel, a solution of cyanogen bromide (CNBr) in water was prepared in a concentration of 67 mg/ml (solution B). A solution of adipic acid dihydrazide (ADH) in 0.5 M NaHCO$_3$ was also prepared at a concentration of 150 mg/ml (solution C). 20 ml of solution A and 0.75 ml of solution C were mixed together to give a preparation with a ratio polysaccharide/CNBr weight/weight that equalled 1. 0.1 N NaOH was added to a pH of 10.8; this pH was maintained during the entire reaction period of 60 minutes. The temperature was about 20° C.

Then the pH was decreased to 8.5 by adding 0.15 ml 0.1 N HCL. 1.17 ml of solution C were added so that the ratio ADH/polysaccharide weight/weight equalled 3.5. The pH was maintained during 15 minutes. Then the reaction mixture was left overnight under stirring at +4° C. 0.1 ml 1 N HCl were added to decrease the pH to 7. The reaction mixture was dialysed against 0.5 M NaCl and then water and subsequently lyophilized.

The size of the derivatized polysaccharide A was controlled on a HLPC exclusion column TSK 4000 (manufacturer Tosohaas). No depolymerization occurred in the course of derivatization.

During the derivatization, about 2.5% of repeat units of polysaccharide A were derivatized with a —NH$_2$ group.

Then the same processes as in example 2 were used to activate the derivatized polysaccharide A and to conjugate the activated polysaccharide A to the peptide as obtained in example 1.

EXAMPLE 5

Comparison of the Conjugate Obtained in Example 2 with Other Products

The utility of the peptide of example 1 as a carrier in a polysaccharide conjugate is demonstrated as follows:

Six-week old NMRI mice received via the sub-cutaneous route one of the following compositions in a volume of 0.5 ml (each injection) and via the intraperitoneal route, in case an adjuvant was used:

(a) 5 µg polysaccharide C (without peptide) at days 1, 15 and 29, in the absence of adjuvant;

(b) 5 µg polysaccharide C (without peptide) together with complete Freund's adjuvant at day 1, and at days 15 and 29 together with incomplete Freund's adjuvant;

(c) 5 µg polysaccharide C and 9 µg peptide together with complete Freund's adjuvant at day 1, and at days 15 and 29 together with incomplete Freund's adjuvant;

(d) the conjugate obtained in example 2 containing 1 µg polysaccharide C and 1.8 µg peptide at days 1, 15 and 29 in the absence of adjuvant;

(e) the conjugate obtained in example 2 containing 5 µg polysaccharide C and 9 µg peptide at days 1, 15 and 29 in the absence of adjuvant;

(f) the conjugate obtained in example 2 containing 5 µg polysaccharide and 9 µg peptide together with complete Freund's adjuvant at day 1, and at days 15 and 29 the conjugate obtained in example 2 together with incomplete Freund's adjuvant; and (g) a conjugate of 5 µg polysaccharide C together with diphtheria anatoxin.

On days 15, 29 and 43 (calculated from the day of the first immunisation), a sample of blood is collected and the antipolysaccharide C antibodies are titrated by ELISA.

The results are summarized in the following table.

TABLE 1

| Compound injected | Dose of polysaccharide injected (µg) | Dose of peptide injected (µg) | Day after immunisation | Sample of blood collected on day | Antibody titer of antipolysaccharide (ELISA unit) |
|---|---|---|---|---|---|
| (a) | 5 |  | 1 | 15 | 10 |
|  |  |  | 15 | 29 | 32 |
|  |  |  | 29 | 43 | 115 |
| (b) | 5 |  | 1 | 15 | 22 |
|  |  |  | 15 | 29 | 39 |
|  |  |  | 29 | 43 | 74 |
| (c) | 5 | 9 | 1 | 15 | 24 |
|  |  |  | 15 | 29 | 34 |
|  |  |  | 29 | 43 | 47 |
| (d) | 1 | 1.8 | 1 | 15 | 32 |
|  |  |  | 15 | 29 | 1052 |
|  |  |  | 29 | 43 | 630 |
| (e) | 5 | 9 | 1 | 15 | 56 |
|  |  |  | 15 | 29 | 321 |
|  |  |  | 29 | 43 | 516 |
| (f) | 5 | 9 | 1 | 15 | 1006 |
|  |  |  | 15 | 29 | 2854 |
|  |  |  | 29 | 43 | 2492 |
| (g) | 5 |  | 1 | 15 | 13 |
|  |  |  | 15 | 29 | 1197 |
|  |  |  | 29 | 43 | 1531 |

The antibody response to non-conjugated polysaccharide C is extremely weak in each case, whereas, the response to polysaccharide C conjugated to either DT or the peptide is satisfactory. With the conjugate of the present invention a booster effect is obtained after the second injection, being an indication for an immune response. The response of the conjugate polysaccharide C—peptide is equivalent to the response obtained with the conjugate of polysaccharide C—DT.

EXAMPLE 6

The conjugate prepared in example 3 with a ratio (w/w) of peptide to polysaccharide of 0.4:1 (corresponding to a ratio of mole peptide per moles repeating units of 1:30) was tested in mice using the same protocol as in example 5. It was immunogenic in mice in the presence of adjuvant and resulted in a booster effect after the second injection. The results can be seen from the following table 2.

TABLE 2

| Compound injected | Dose of polysaccharide injected (µg) | Dose of peptide injected (µg) | Day after immunisation | Sample of blood collected on day | Antipolysaccharide Pn4 (ELISA unit) |
|---|---|---|---|---|---|
| Pneumo type 4 Ps + adjuv. | 5 |  | 1 | 15 | <10 |
|  |  |  | 15 | 29 | <10 |
|  |  |  | 29 | 43 | <10 |
| Pneumo type 4 Ps + peptide + adjuv. | 5 | 1.9 | 1 | 15 | ~18 |
|  |  |  | 15 | 29 | ~24 |
|  |  |  | 29 | 43 | <10 |

TABLE 2-continued

| Compound injected | Dose of polysaccharide injected (μg) | Dose of peptide injected (μg) | Day after immunisation | Sample of blood collected on day | Anti-polysaccharide Pn4 (ELISA unit) |
|---|---|---|---|---|---|
| Conj. Pn4-peptide-1 + adjuv. | 5 | 1.9 | 1 | 15 | ~61 |
| | | | 15 | 29 | 458 |
| | | | 29 | 43 | 2601 |
| Saline | | | 1 | 15 | <10 |
| | | | 15 | 29 | <10 |
| | | | 29 | 43 | <10 |

What is claimed is:

1. A conjugate comprising a peptide moiety and a polysaccharide moiety, said peptide moiety having an N-terminal amino acid residue, a C-terminal amino acid residue, and an amino acid sequence from said N-terminal amino acid residue to said C-terminal amino acid residue, wherein the amino acid sequence consists of 40 to 200 residues and comprises a region of from 35 to 104 amino acids in a sequence selected from the group consisting of amino acid sequences:

(a) of SEQ ID NO. 1, beginning with the amino acid residue in any one of positions 1 to 5 and ending with the amino acid residue in any one of positions 40 to 104;
   (b) of SEQ ID NO. 2, beginning with the amino acid residue in any one of positions 1 to 5 and ending with the amino acid residue in any one of positions 40 to 104;
   (c) of SEQ ID NO. 3, beginning with the amino acid residue in any one of positions 1 to 5 and ending with the amino acid residue in any one of positions 40 to 104;
   (d) of SEQ ID NO. 4, beginning with the amino acid residue in any one of positions 1 to 5 and ending with the amino acid residue in any one of positions 40 to 104; and
   (e) of SEQ ID NO. 5, beginning with the amino acid residue in any one of positions 1 to 5 and ending with the amino acid residue in any one of positions 40 to 104.

2. The conjugate of claim 1, wherein the peptide moiety consists of at least 40 amino acids of the amino acid sequence shown in SEQ ID NO. 1, beginning with the amino acid residue in any one of positions 1 to 5 and ending with the amino acid residue in any one of positions 40 to 104.

3. The conjugate of claim 1, wherein the peptide moiety consists of a sequence of at least 70 amino acid residues having an amino acid sequence that is identical to an amino acid sequence of SEQ ID NO. 1, SEQ ID NO. 2, SEQ ID NO. 3, SEQ ID NO. 4, or SEQ ID NO. 5 beginning with the amino acid residue in any one of positions 1 to 5 and ending with the amino acid residue in any one of the positions 70 to 104.

4. The conjugate of claim 1, wherein the peptide moiety consists of a sequence of at least 100 amino acid residues having an amino acid sequence that is identical to an amino acid sequence of SEQ ID NO. 1, SEQ ID NO. 2, SEQ ID NO. 3, SEQ ID NO. 4, or SEQ ID NO. 5 beginning with the amino acid residue in any one of the positions 1 to 5 and ending with the amino acid residue in any one of the positions 100 to 104.

5. The conjugate of claim 1, wherein the peptide moiety consists of the amino acid sequence of SEQ ID NO. 1.

6. The conjugate of claim 1, wherein the peptide moiety further comprises an additional cysteine residue.

7. The conjugate of claim 6, wherein the cysteine residue is located at one terminus of the peptide sequence.

8. The conjugate of claim 1, further comprising an additional cysteine residue in the peptide moiety, and a bifunctional linker, wherein the peptide moiety is bonded to the linker via the thiol group of the cysteine and the polysaccharide moiety is bonded to the other functional group of the linker via a hydroxy, carboxy, or amino group.

9. The conjugate of claim 1, wherein the conjugate comprises one mole of peptide per 50 to 1 moles of polysaccharide.

10. A method of forming a conjugate, comprising linking a peptide to a polysaccharide, thereby forming a polysaccharide-peptide conjugate, wherein the peptide has an N-terminal amino acid residue, a C-terminal amino acid residue, and an amino acid sequence from said N-terminal amino acid residue to said C-terminal amino acid residue, and wherein the amino acid sequence consists of 40 to 200 residues and comprises a region of 35 to 104 amino acids in sequence being identical to an amino acid sequence selected from the group consisting of amino acid sequences:

(a) of SEQ ID NO. 1, beginning with the amino acid residue in any one of positions 1 to 5 and ending with the amino acid residue in any one of positions 40 to 104;
   (b) of SEQ ID NO. 2, beginning with the amino acid residue in any one of positions 1 to 5 and ending with the amino acid residue in any one of positions 40 to 104;
   (c) of SEQ ID NO. 3, beginning with the amino acid residue in any one of positions 1 to 5 and ending with the amino acid residue in any one of positions 40 to 104;
   (d) of SEQ ID NO. 4, beginning with the amino acid residue in any one of positions 1 to 5 and ending with the amino acid residue in any one of positions 40 to 104; and
   (e) of SEQ ID NO. 5, beginning with the amino acid residue in any one of positions 1 to 5 and ending with the amino acid residue in any one of positions 40 to 104.

11. The method of claim 10, wherein the polysaccharide is selected from the group of polysaccharides consisting of lipopolysaccharides, O-antigens, bacterial membrane polysaccharides, capsular membrane polysaccharides and fungal membrane polysaccharides.

12. An immunogenic composition comprising the conjugate of claim 1 and a pharmaceutically acceptable carrier, excipient, or diluent.

* * * * *

SEQUENCE LISTING

<160> NUMBER OF SEQ ID NOS: 5

<210> SEQ ID NO 1
<211> LENGTH: 104
<212> TYPE: PRT
<213> ORGANISM: Neisseria meningitidis

<400> SEQUENCE: 1

Leu Tyr Tyr Lys Asn Tyr Arg Tyr Tyr Ala Leu Lys Ser Gly Gly Ser
 1               5                  10                  15

Val Asn Ala Pro Met Pro Glu Asn Gly Gln Thr Glu Asn Asn Asp Trp
            20                  25                  30

Ile Leu Met Gly Ser Thr Gln Glu Glu Ala Lys Lys Asn Ala Met Asn
        35                  40                  45

His Lys Asn Asn Gln Arg Ile Ser Gly Phe Ser Gly Phe Phe Gly Glu
    50                  55                  60

Glu Asn Gly Lys Gly His Asn Gly Ala Leu Asn Leu Asn Phe Asn Gly
65                  70                  75                  80

Lys Ser Ala Gln Asn Arg Phe Leu Leu Thr Gly Gly Thr Asn Leu Asn
                85                  90                  95

Gly Lys Ile Ser Val Thr Gln Gly
            100

<210> SEQ ID NO 2
<211> LENGTH: 104
<212> TYPE: PRT
<213> ORGANISM: Neissseria meningitidis

<400> SEQUENCE: 2

Leu Tyr Tyr Lys Asn Tyr Arg Tyr Tyr Ala Leu Lys Ser Gly Gly Ser
 1               5                  10                  15

Val Asn Ala Pro Met Pro Glu Asn Gly Val Thr Glu Asn Asn Asp Trp
            20                  25                  30

Val Phe Met Gly Tyr Thr Gln Glu Glu Ala Lys Lys Asn Ala Met Asn
        35                  40                  45

His Lys Asn Asn Gln Arg Ile Ser Gly Phe Ser Gly Phe Phe Gly Glu
    50                  55                  60

Glu Asn Gly Lys Gly His Asn Gly Ala Leu Asn Leu Asn Phe Asn Gly
65                  70                  75                  80

Lys Ser Ala Gln Asn Arg Phe Leu Leu Thr Gly Gly Thr Asn Leu Asn
                85                  90                  95

Gly Lys Ile Ser Val Thr Gln Gly
            100

<210> SEQ ID NO 3
<211> LENGTH: 104
<212> TYPE: PRT
<213> ORGANISM: Neisseria meningitidis

<400> SEQUENCE: 3

Leu Tyr Tyr Lys Asn Tyr Arg Tyr Tyr Ala Leu Lys Ser Gly Gly Ser
1               5                   10                  15

Val Asn Ala Pro Met Pro Glu Asn Gly Gln Thr Glu Asn Asn Asp Trp
            20                  25                  30

Val Phe Met Gly Tyr Lys Gln Glu Glu Ala Gln Lys Asn Ala Met Asn
        35                  40                  45

His Lys Asn Asn Gln Arg Ile Ser Gly Phe Ser Gly Phe Phe Gly Glu
    50                  55                  60

Glu Asn Gly Lys Gly His Asn Gly Ala Leu Asn Leu Asn Phe Asn Gly
65                  70                  75                  80

Lys Ser Ala Gln Asn Arg Phe Leu Leu Thr Gly Gly Thr Asn Leu Asn
                85                  90                  95

Gly Lys Ile Ser Val Thr Gln Gly
            100

<210> SEQ ID NO 4
<211> LENGTH: 104
<212> TYPE: PRT
<213> ORGANISM: Neisseria gonorrhoeae

<400> SEQUENCE: 4

Leu Tyr Tyr Lys Asn Tyr Arg Tyr Tyr Ala Leu Lys Ser Gly Gly Arg
1               5                   10                  15

Leu Asn Ala Pro Met Pro Glu Asn Gly Val Ala Glu Asn Asn Asp Trp
            20                  25                  30

Val Phe Met Gly Tyr Thr Gln Glu Glu Ala Arg Lys Asn Ala Met Asn
        35                  40                  45

Asn Lys Asn Asn Arg Arg Ile Gly Asp Phe Gly Gly Phe Phe Asp Glu
    50                  55                  60

Glu Asn Gly Lys Gly His Asn Gly Ala Leu Asn Leu Asn Phe Asn Gly
65                  70                  75                  80

Lys Ser Ala Gln Asn Arg Phe Leu Leu Thr Gly Gly Ala Asn Leu Asn
                85                  90                  95

Gly Gly Asn Gly Arg Pro Val Lys
            100

<210> SEQ ID NO 5
<211> LENGTH: 104
<212> TYPE: PRT
<213> ORGANISM: Neisseria gonorrheae

<400> SEQUENCE: 5

Leu Tyr Tyr Lys Asn Tyr Arg Tyr Tyr Ala Leu Lys Ser Gly Gly Arg
1               5                   10                  15

Leu Asn Ala Pro Met Pro Glu Asn Gly Val Ala Glu Asn Asn Asp Trp
            20                  25                  30

-continued

```
Ile Phe Met Gly Tyr Thr Gln Glu Glu Ala Arg Lys Asn Ala Met Asn
            35                  40                  45

His Lys Asn Asn Arg Arg Ile Gly Asp Phe Gly Gly Phe Phe Asp Glu
        50                  55                  60

Glu Asn Gly Lys Gly His Asn Gly Ala Leu Asn Leu Asn Phe Asn Gly
 65              70                  75                  80

Lys Ser Ala Gln Asn Arg Phe Leu Leu Thr Gly Gly Ala Asn Leu Asn
                85                  90                  95

Gly Lys Ile Ser Val Thr Gln Gly
             100
```